United States Patent

Fujiwara et al.

[11] Patent Number: 5,849,787
[45] Date of Patent: Dec. 15, 1998

[54] HYPERCHOLESTEROLEMIA THERAPEUTIC AGENT

[75] Inventors: Mutsunori Fujiwara, Tokyo; Toru Hiyoshi, Yokohama; Shinzo Makita, Kanagawa-Ken, all of Japan

[73] Assignee: Mutsunori Fujiwara, Tokyo, Japan

[21] Appl. No.: 871,944

[22] Filed: Jun. 10, 1997

Related U.S. Application Data

[63] Continuation of Ser. No. 603,778, Feb. 20, 1996, Pat. No. 5,705,526.

[30] Foreign Application Priority Data

Jun. 15, 1995 [JP] Japan .................................. 7-172874

[51] Int. Cl.⁶ .................. A61K 31/355; A61K 31/01; A61K 31/015
[52] U.S. Cl. .................. 514/458; 514/762; 514/763; 514/824
[58] Field of Search .................. 514/458, 762, 514/763, 824

[56] References Cited

PUBLICATIONS

CA 122:54905, Becker et al, 1994.
CA 82:29985, Erdman et al. (1974).
AU: Zhang–LX; Source: Carcinogenesis 1991 Nov; 12(11):2109–149.
AU: Rousseau–EJ; SO: Free–Radic–Biol–Med. 1992 Oct; 13(4):407–33.
Erdman et al., Nutrition Reports International, vol. 10, No. 5, pp. 277–284 (Nov. 1974).

*Primary Examiner*—Kimberly Jordan
*Attorney, Agent, or Firm*—Birch, Stewart, Kolasch & Birch, LLP

[57] ABSTRACT

A hypercholesterolemia therapeutic agent containing lycopene as an effective ingredient. The hypercholesterolemia therapeutic agent comprises a soft-capsulated drug, and the soft-capsulated drug comprises a soft capsule which comprises gelatin and glycerin, and contents which comprise lycopene, β-carotene, α-carotene, d-α tocopherol and a mixture of a wheat germ oil and a vegetable oil, which contents are packed into the soft capsule.

2 Claims, No Drawings

HYPERCHOLESTEROLEMIA THERAPEUTIC AGENT

This application is a continuation of application Ser. No. 08/603,778, filed on Feb. 20, 1996, now U.S. Pat. No. 5,705,526, the entire contents of which are hereby incorporated by reference.

As far as we know, there are available the following prior art documents pertinent to the present invention:

(1) SilverPlatter v 2.15 MEDLINE (R) 1991 12 of 23, Carcinogenesis. 1991 Nov. 12(11), pp. 2109–2114; and (2) SilverPlatter v 2.15 MEDLINE (R) 1992 14 of 27, Free-Radic-Biol-Med. 1992 Oct. 13(4), pp. 407–433.

The contents of the prior art disclosed in the above-mentioned prior art documents will be discussed hereafter under the heading of the "BACKGROUND OF THE INVENTION".

BACKGROUND OF THE INVENTION (Field of the Invention)

The present invention relates to a hypercholesterolemia therapeutic agent.

(Related Art Statement)

Hypercholesterolemia is a morbidity in which a cholesterol concentration in blood continues to be excessively high, and is an important factor which accelerates an arteriosclerotic transformation in various organs. A grave hypercholesterolemia causes serious complications including ischemic cardiac maladies such as myocardial infarction, cerebral infarction and cerebral hemorrhage caused by cerebral arteriosclerosis, and lower-extremity gangrene caused by lower-extremity-obstructive arteriosclerosis and the like.

In hypercholesterolemia, a long period of continuance of a total cholesterol concentration of at least 220 mg/dl in serum is believed to accelerate an arteriosclerotic transformation. Most of cholesterol in blood is present in the forms of low-density lipoprotein (LDL), high-density lipoprotein (HDL), very-low-density lipoprotein (VLDL) and chylomicron, and the balance is present in the form of free cholesterol. The above-mentioned total cholesterol concentration means a total amount of cholesterol obtained by converting all the above-mentioned forms of cholesterol into the form of free cholesterol.

Particularly, the concentration of a low-density lipoprotein (LDL) fraction in blood exerts a large effect on an arteriosclerotic transformation. It is furthermore known that foamy cells are observed in an initial focus of arteriosclerosis. Low-density lipoprotein (LDL) is an essential substance which is incorporated from LDL receptors into peripheral tissues of a heart, muscles and the like to serve as a material for a cell membrane. However, if present in excess, low-density lipoprotein (LDL), which tends to precipitate onto blood vessel walls, accumulates thereon, is incorporated into macrophages, and causes a change of macrophages into foamy cells, thus resulting in the formation of a focus of arteriosclerosis.

Hypercholesterolemia therapeutic agents practically applied at present include: (1) a hydroxy-methylglutaryl-CoA (HMG-CoA) reductase inhibitor (pravastatin, for example) which restrains synthesis of cholesterol, (2) probucol which mainly promotes catabolism from cholesterol to a bile acid and excretion thereof, (3) an anion exchange resin which mainly restrains absorption of cholesterol and promotes excretion of a bile acid (cholestyramine, for example), and (4) a clofibrate-type drug (clofibrate, for example).

When using these therapeutic agents, however, since there are delicate differences between adaptive symptoms relative to these therapeutic agents depending upon the type of hypercholesterolemia, it is necessary to appropriately select a therapeutic agent which is the most effective on the particular adaptive symptom. Selection of the effective therapeutic agent should be made also in response to the occurrence of complications and side effects which may take place along with the use of the therapeutic agent. When a symptom cannot be sufficiently controlled by a single kind of therapeutic agent, furthermore, a plurality of therapeutic agents having different action mechanisms should be employed in combination.

Under such circumstances, there is a strong demand for development of a novel hypercholesterolemia therapeutic agent capable of overcoming the above-mentioned problems, but such a hypercholesterolemia therapeutic agent has not as yet been proposed.

A main effective ingredient of the hypercholesterolemia therapeutic agent of the present invention is lycopene as described later, and the following documents are available as prior art documents regarding lycopene:

(1) SilverPlatter v 2.15 MEDLINE (R) 1991 12 of 23, Carcinogenesis, 1991 Nov. 12 (11), pp. 2109–2114 (hereinafter referred to as the "prior art 1"); and (2) SilverPlatter v 2.15 MEDLINE (R) 1992 14 of 27, Free-Radic-Biol-Med. 1992 Oct. 13 (4), pp. 407–433 (hereinafter referred to as the "prior art 2").

However, the prior arts 1 and 2 disclose only the findings that lycopene, which is a kind of carotenoids, serves in an organism as a radical scavenger like the other carotenoids to deactivate active oxygen, and prevents the occurrence of a tissue handicap or a cancer caused by active oxygen.

SUMMARY OF THE INVENTION

An object of the present invention is therefore to provide a novel hypercholesterolemia therapeutic agent free from side effects.

In accordance with one of the features of the present invention, there is provided a hypercholesterolemia therapeutic agent which contains lycopene as an effective ingredient.

In accordance with another one of the features of the present invention, there is provided a hypercholesterolemia therapeutic agent, wherein:

said hypercholesterolemia therapeutic agent comprises a soft-capsulated drug, and said soft-capsulated drug comprises a soft capsule which comprises gelatin and glycerin, and contents which comprise lycopene, β-carotene, α-carotene, d-α tocopherol and a mixture of a wheat germ oil and a vegetable oil, which contents are packed into said soft capsule.

In accordance with further another one of the features of the present invention, there is provided a method for administering a hypercholesterolemia therapeutic agent, which comprises:

upon using a hypercholesterolemia therapeutic agent containing lycopene as an effective ingredient, administering said lycopene in an amount within a range of from 3 to 15 mg per day per adult.

DETAILED DESCRIPTION OF PREFERRED EMBODIMENTS

From the above-mentioned point of view, extensive studies were carried out to develop a novel hypercholesterolemia therapeutic agent free from side effects.

As a result, the following findings were obtained during the course of a study on the physiological effect of lycopene: a cholesterol concentration in blood decreases when lycopane is administered to an organism, and particularly, a concentration of low-density lipoprotein (LDL) in blood, which has a large influence on an arteriosclerotic transformation, among other kinds of lipoprotein containing cholesterol, considerably decreases.

The present invention was made on the basis of the above-mentioned findings, and a hypercholesterolemia therapeutic agent of the present invention is characterized in that it contains lycopene as an effective ingredient.

When administered to an organism, lycopene has a function of considerably decreasing a cholesterol concentration in blood. Particularly, lycopene has a function of remarkably decreasing a concentration of low-density lipoprotein (hereinafter referred to as "LDL") in blood, which has a large influence on an arteriosclerotic transformation, among other kinds of lipoprotein containing cholesterol. Lycopene is therefore very important as an effective ingredient of a hypercholesterolemia therapeutic agent. Lycopene has on the other hand a property of tending to be very easily oxidized.

Lycopene, which is an effective ingredient of the hypercholesterolemia therapeutic agent of the present invention is a known substance, and is expressed by the following chemical formula:

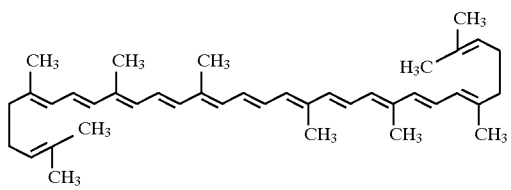

Lycopene is contained in a large amount generally in fully ripe fruit, especially in a fully ripe tomato. As a method for obtaining lycopene, there is known a method called the solvent extraction method which comprises usually using a fully ripe tomato as a raw material, and extracting lycopene therefrom by the use of a solvent such as ethyl acetate, normal hexane, or acetone.

Lycopene may directly be administered to an organism. Lycopene may also be appropriately formulated and the formulated lycopene may be administered to an organism through any of various paths. When orally administered, lycopene alone may directly be administered as the hypercholesterolemia therapeutic agent of the present invention. As required, furthermore, an excipient, a binding agent, a disintegrant, a glossing agent, a coating agent, an emulsifier, a dispersant, a solvent, or a stabilizer may be added to lycopene to formulate into a tabular drug, a granular drug, a pulverulent drug, a powdery drug, a capsulated drug or a soft-capsulated drug.

The hypercholesterolemia therapeutic agent comprising a soft-capsulated drug comprises a soft capsule which comprises gelatin and glycerin, and contents of such a soft capsule, which comprise lycopene, β-carotene, α-carotene, d-α tocopherol and a mixture of a wheat germ oil and a vegetable oil.

It suffices to orally administer lycopene in an amount within a range of from 1 to 25 mg per day per adult, which amount is appropriately increased or decreased, depending upon a symptom. An amount of oral administration of lycopene should more preferably be within a range of from 3 to 15 mg per day per adult. With an amount of oral administration of under 1 mg, a desired effect is unavailable. Even with an amount of oral administration of over 25 mg, on the other hand, the function of lycopene of remarkably decreasing an LDL concentration in blood is saturated. When administering to a large organism, an amount of oral administration of lycopene may be within a range of from 1 to 50 mg per day.

In the soft-capsulated drug, β-carotene, α-carotene and d-α tocopherol used together with lycopene have a function of complementing the lycopene's function of remarkably decreasing an LDL concentration in blood, respectively, and have also a function of preventing lycopene from being oxidized by oxygen mixed into the soft-capsulated drug.

The amount of oral administration of β-carotene is within a range of from 1 to 12.5 mg per day per adult. The amount of oral administration of α-carotene is within a range of from 1 to 12.5 mg per day per adult. The amount of oral administration of d-α tocopherol is within a range of from 1 to 17 mg per day per adult.

The mixture of a wheat germ oil and a vegetable oil has a function of improving fluidity of the contents of the soft-capsulated drug. The amount of the mixture of the wheat germ oil and the vegetable oil may appropriately be adjusted depending upon the size of a soft capsule.

In the above-mentioned administration of lycopene, while the amount of the contents of the soft-capsulated drug, if the soft-capsulated drug is used, varies depending upon the size of the soft capsule, the amount of lycopene in the soft-capsulated drug is usually within a range of from 1 to 25 mg. The amount of lycopene in the soft-capsulated drug, which is administered to a large organism, may be within a range of from 1 to 50 mg.

The amount of β-carotene in the soft-capsulated drug is within a range of from 1 to 12.5 mg. The amount of α-carotene in the soft-capsulated drug is within a range of from 1 to 12.5 mg. The amount of d-α tocopherol in the soft-capsulated drug is within a range of from 1 to 17 mg.

Now, the hypercholesterolemia therapeutic agent of the present invention is described further in detail by means of an example.

EXAMPLE

A lycopene stock solution was prepared in accordance with the following procedure, and then a soft-capsulated drug containing lycopene was manufactured:

(1) Preparation of lycopene stock solution (i.e., oleoresin containing 5% lycopene):

First, fully ripe tomatoes originating in Israel were crushed, and a tomato oil and lycopene dissolved in the tomato oil were extracted together by the use of ethyl acetate as a solvent. Then, ethyl acetate was evaporated from the resultant extraction solution to prepare a lycopene stock solution having the following chemical composition:

lycopene: 5 wt. %, and tomato oil: 95 wt. %.

(2) Manufacture of soft-capsulated drug containing lycopene:

First, raw materials were weighed so as to achieve the following weight ratios, and these raw materials were mixed to prepare contents of a soft-capsulated drug:

wheat germ oil: 257 mg, soy bean oil containing vitamin E: 8 mg, lycopene stock solution: 30 mg, and
palm oil carotene (containing β-carotene and α-carotene): 5 mg,
   total: 300 mg.

On the other hand, edible gelatin added with water was heated to melt same, and the resultant melt was mixed with glycerin to prepare a raw material for a soft capsule.

Then, while feeding a thin sheet prepared from the above-mentioned raw material for a soft capsule to a rotary-type capsuling machine, the above-mentioned contents of the soft-capsulated drug were fed onto the thus prepared thin sheet by means of a metering pump, thus manufacturing a soft-capsulated drug containing lycopene. The resultant soft-capsulated drug had the following chemical composition:

Chemical composition of the contents per particle:
lycopene: 1.5 mg,
β-carotene: 1.0 mg,
α-carotene: 0.5 mg,
d-α tocopherol: 5.0 mg, and
mixture of wheat germ oil and vegetable oil: 292.0 mg,
   total: 300.0 mg,
and,
Chemical composition of the soft capsule per particle:
gelatin: 127.5 mg,
and
glycerin: 22.5 mg,
   total: 150.0 mg.

In this example, β-carotene, α-carotene and d-α tocopherol were added as antioxidants.

(3) Administration test:

A test was carried out by administering the soft-capsulated drug containing lycopene obtained in this example to healthy adults. The test was applied to 19 subjects in total comprising ten male subjects (an average age of 52.1, an average height of 166.1 cm, and an average weight of 69.15 kg) and nine female subjects (an average age of 50.0, an average height of 155.67 cm, and an average weight of 58.5 kg).

Two particles of soft-capsulated drug were administered twice a day in the morning and evening (resulting in an amount of lycopene administration of 3 mg in one administration and 6 mg per day) to each of these 19 subjects for a period of 29 days.

Before the start of administration and after the completion of administration, blood was sampled from each of these 19 subjects to carry out a blood chemical inspection. Inspection items included the respective concentrations of lycopene, LDL, high-density lipoprotein (hereinafter referred to as "HDL") and total cholesterol in serum. The lycopene concentration was measured by the HPLC method (the abbreviation of High Performance Liquid Chromatography method). The LDL concentration was measured by the heparin $Ca^{2+}$ precipitation method. The HDL concentration was measured by the polyanion precipitation method. The HDL concentration was a value calculated by converting the concentration of cholesterol contained in the HDL fraction into a concentration of free cholesterol. The total cholesterol concentration was measured by the oxygen method. The total cholesterol concentration was a value calculated by converting the concentration of cholesterol contained in all the fractions in serum into a concentration of free cholesterol.

Table 1 shows an outline of the subjects, and Table 2, the results of the blood chemical inspections before the start of administration and after the completion of administration. The abbreviations in Table 2 have the following meanings: reti-p being retinol palmitate, GOT being glutamic-oxaloacetic transaminase, GPT being glutamic-pyruvic transaminase, LDH being lactate dehydrogenase, ALP being alkaline phosphatase, γ-GTP being glutamyl transferase, BUN being blood urea nitrogen, and VLDL being very-low-density lipoprotein.

TABLE 1

|  | Age | Height (cm) | Weight (kg) |
|---|---|---|---|
| Male (n = 10) | 52.1 ± 9.95 | 166.1 ± 4.48 | 69.15 ± 7.02 |
| Female (n = 9) | 50.0 ± 5.17 | 155.67 ± 3.74 | 58.5 ± 12.22 |
| Total (n = 19) | 51.11 ± 5.55 | 161.16 ± 6.70 | 64.11 ± 10.99 |

TABLE 2 (1)

|  |  | Before the start of administration | After the completion of administration |
|---|---|---|---|
| Lycopene | (μg/dl) | 17.87 ± 9.83 | 29.92 ± 9.23 |
| LDL | (mg/dl) | 541.16 ± 159.0 | 510.16 ± 153.67 |
| VLDL | (mg/dl) | 146.95 ± 93.0 | 167.9 ± 97.0 |
| Total cholesterol | (mg/dl) | 207.05 ± 32.42 | 205.47 ± 32.24 |
| HDL | (mg/dl) | 52.32 ± 12.39 | 56.74 ± 13.02 |
| Triglyceride | (mg/dl) | 109.63 ± 71.83 | 120.58 ± 73.84 |
| Vitamin A | (IU/dl) | 210.16 ± 59.44 | 191.53 ± 53.85 |
| Retinol | (μg/dl) | 53.59 ± 14.32 | 53.93 ± 17.93 |
| reti-P | (μg/dl) | 2.34 ± 0.7 | 4.56 ± 8.13 |
| Retinol-binding protein | (mg/dl) | 4.64 ± 1.41 | 4.81 ± 1.16 |
| β-carotene | (μg/dl) | 60.57 ± 30.61 | 123.08 ± 46.91 |
| Prealbumin | (mg/dl) | 31.57 ± 5.87 | 31.16 ± 5.24 |
| Lipoprotein | (a)(mg/dl) | 20.11 ± 20.81 | 20.11 ± 21.93 |
| Apolipoprotein A-I | (mg/dl) | 142.74 ± 25.48 | 143.11 ± 23.0 |
| Apolipoprotein B | (mg/dl) | 107.11 ± 33.54 | 112.0 ± 34.09 |
| Apolipoprotein E | (mg/dl) | 5.06 ± 1.06 | 5.27 ± 0.92 |

TABLE 2 (2)

|  |  | Before the start of administration | After the completion of administration |
|---|---|---|---|
| Remnant-like particles | (mg/dl) | 3.51 ± 3.23 | 3.56 ± 2.62 |
| GOT | (IU)/l | 25.32 ± 17.13 | 26.84 ± 21.68 |
| GPT | (IU)/l | 28.32 ± 29.38 | 28.16 ± 29.17 |
| LDH | (IU)/l | 378.95 ± 70.5 | 389.63 ± 62.77 |
| ALP | (IU)/l | 147.9 ± 33.69 | 144.68 ± 29.83 |
| γ-GTP | (IU)/l | 53.42 ± 78.13 | 49.21 ± 51.0 |
| Choline esterase | (pH) | 1.07 ± 0.2 | 1.04 ± 0.18 |
| Amylase | (IU)/l | 107.26 ± 34.66 | 101.32 ± 35.39 |
| Creatine kinase | (IU)/l | 124.74 ± 54.87 | 110.63 ± 44.13 |
| Total protein in serum | (g/dl) | 7.41 ± 0.39 | 7.44 ± 0.38 |
| Albumin | (g/dl) | 4.47 ± 0.17 | 4.44 ± 0.16 |
| BUN | (mg/dl) | 18.42 ± 3.72 | 16.95 ± 3.66 |
| Creatinine | (mg/dl) | 0.83 ± 0.18 | 0.84 ± 0.16 |
| uric acid | (mg/dl) | 5.33 ± 0.98 | 5.45 ± 1.42 |
| Ca | (mg/dl) | 9.06 ± 0.55 | 9.02 ± 0.46 |
| Inorganic phosphorus | (mg/dl) | 3.13 ± 0.37 | 3.08 ± 0.5 |
| Na | (mEq/l) | 142.42 ± 1.77 | 142.0 ± 1.73 |
| K | (mEq/l) | 4.16 ± 0.22 | 4.12 ± 0.27 |

TABLE 2 (3)

|  |  | Before the start of administration | After the completion of administration |
|---|---|---|---|
| Glucose | (mg/dl) | 100.21 ± 9.79 | 98.90 ± 10.89 |
| Hemoglobin A1c | (%) | 5.57 ± 0.36 | 5.51 ± 0.45 |
| Leukocyte | (×1/ml) | 5868.42 ± 1268.88 | 6063.16 ± 1133.93 |

TABLE 2 (3)-continued

|  |  | Before the start of administration | After the completion of administration |
|---|---|---|---|
| Erythrocyte | (×10⁴/ml) | 440.53 ± 34.84 | 443.11 ± 31.98 |
| Hemoglobin | (g/dl) | 13.33 ± 1.30 | 13.28 ± 1.14 |
| Platelet | (×10⁴/ml) | 24.07 ± 5.87 | 25.05 ± 6.06 |

According to the results of the administration test, the LDL concentration in serum, as shown in Table 2(1), while being 541.16±159.0 mg/dl before the start of administration, decreased to 510.16±153.67 mg/dl after the completion of administration. In other words, the LDL concentration in serum was reduced by 31 mg/dl on an average, i.e., by about 5.5% on an average relative to the LDL concentration in serum before the start of administration, under the effect of the administration of lycopene. For these results, a significant difference at a level of significance P<0.05% was observed in the Student t-test.

On the other hand, the HDL concentration in serum, as shown in Table 2(1), while being 52.32±12.39 mg/dl before the start of administration, increased to 56.74±13.02 mg/dl after the completion of administration. In other words, the HDL concentration in serum showed an increasing tendency under the effect of the administration of lycopene. Furthermore, the total cholesterol concentration in serum, as shown also in table 2(1), while being 207.05±32.42 mg/dl before the start of administration, decreased to 205.47±32.24 mg/dl after the completion of administration. In other words, the total cholesterol concentration in serum showed a decreasing tendency under the effect of the administration of lycopene. Occurrence of side effects was not observed.

It was clearly recognized from the above-mentioned results that lycopene considerably reduced the concentration in blood of LDL which had a function of transmitting cholesterol to peripheral tissues so as to increase the amount of cholesterol in blood, and simultaneously, that lycopene increased the concentration in blood of HDL whch had a function of transmitting cholesterol from peripheral tissues to the liver so as to reduce the amount of cholesterol in blood, whereby lycopene eventually reduced the total amount of cholesterol in blood. In addition, it was judged that administration of lycopene caused no side effect.

As described above in detail, lycopene largely reduces the concentration in blood of LDL which exerts a large effect on an arteriosclerotic transformation, and simultaneously, increases the concentration in blood of HDL which has a function of reducing cholesterol in blood. In addition, lycopene causes no side effect. The hypercholesterolemia therapeutic agent of the present invention containing lycopene as an effective ingredient brings about a very excellent effects.

What is claimed is:

1. A hypercholesterolemia therapeutic agent comprising a soft-capsulated drug, having a function of reducing a concentration in blood of LDL and increasing a concentration in blood of HDL, which comprises:

a soft capsule comprising gelatin and glycerin, and contents packed into said soft capsule, which contents consist essentially of:

lycopene: from 1 to 25 mg,

β-carotene: from 1 to 12.5 mg,

α-carotene: from 1 to 12.5 mg, d-α tocopherol: from 1 to 17 mg, and a mixture of a wheat germ oil and a vegetable oil.

2. The hypercholesterolemia therapeutic agent of claim 1, wherein said contents of said soft-capsulated drug consist essentially of:

lycopene: 1.5 mg,

β-carotene: 1.0 mg,

α-carotene: 0.5 mg, d-α tocopherol: 5.0 mg, and said mixture of said wheat germ oil and said vegetable oil: 292.0 mg; and said soft capsule consists essentially of:

gelatin: 127.5 mg, and glycerin: 22.5 mg.

\* \* \* \* \*